United States Patent
Broderick et al.

(10) Patent No.: US 11,091,454 B2
(45) Date of Patent: Aug. 17, 2021

(54) PROCESS FOR THE SYNTHESIS OF AROMATIC DICARBOXYLIC ACIDS

(71) Applicant: UOP LLC, Des Plaines, IL (US)

(72) Inventors: Erin Marie Broderick, Arlington Heights, IL (US); Hayim Abrevaya, Wilmette, IL (US); Paul T. Barger, Arlington Heights, IL (US); Alakananda Bhattacharyya, Glen Ellyn, IL (US)

(73) Assignee: UOP LLC, Des Plaines, IL (US)

( * ) Notice: Subject to any disclaimer, the term of this patent is extended or adjusted under 35 U.S.C. 154(b) by 72 days.

(21) Appl. No.: 16/586,942

(22) Filed: Sep. 28, 2019

(65) Prior Publication Data
US 2021/0094928 A1    Apr. 1, 2021

(51) Int. Cl.
*C07D 307/68*    (2006.01)

(52) U.S. Cl.
CPC .................. *C07D 307/68* (2013.01)

(58) Field of Classification Search
CPC .................................................. C07D 307/68
See application file for complete search history.

(56) References Cited

U.S. PATENT DOCUMENTS 10,160,740 B2    12/2018    Kanan et al.

OTHER PUBLICATIONS

Luo & Larrosa, C—H Carboxylation of Aromatic Compounds through CO2 Fixation, 10 ChemSusChem 3317-3332 (2017) (Year: 2017).*

* cited by examiner

*Primary Examiner* — Timothy R Rozof
(74) *Attorney, Agent, or Firm* — Paschall & Associates, LLC; Mark Goldberg

(57) ABSTRACT

A method is provided for synthesizing an aromatic carboxylic acid compound comprising providing an aromatic compound or an aromatic compound with at least one carboxylic group; providing a metal hydroxide and at least one carboxylate to produce a mixture; and adding carbon dioxide to the mixture under pressures from about atmospheric to 1000 psig and sufficient heat for a time sufficient to produce aromatic carboxylic acid compounds. The aromatic carboxylic acid compounds may include terephthalic acid, naphthalic acid, thiophene dicarboxylic acid, pyridine dicarboxylic acid, carbazole dicarboxylic acid, and dibenzothiophene dicarboxylic acid.

18 Claims, No Drawings

PROCESS FOR THE SYNTHESIS OF AROMATIC DICARBOXYLIC ACIDS

This disclosure relates generally to a process for the production of aromatic carboxylic acid compounds including 2,5-furandicarboxylic acid from pentoses from biomass with the use of inexpensive reagents.

In accordance with this disclosure is provided a method for synthesizing furan-2,5-dicarboxylate (FDCA) which may be used as a starting material for a family of biobased plastics as a replacement for such starting materials as terephthalic acid and p-xylene. A current route to FDCA converts fructose to FDCA through an intermediate, hydroxymethylfurfural (HMF). This route has disadvantages that lead to an expensive product (including the issues that fructose is an expensive starting material and that HMF has stability issues). A new route through pentoses from biomass could eliminate the challenges of the current route and use carbon dioxide, which is a greenhouse gas, as a reagent. It is desirable to provide a method that uses less expensive starting materials.

SUMMARY

A method for synthesizing an aromatic carboxylic acid compound is provided comprising providing an aromatic compound or an aromatic compound with at least one carboxylic group; providing a metal hydroxide and at least one carboxylate to produce a mixture; and adding carbon dioxide to the mixture under pressures from about atmospheric to 1000 psig and sufficient heat for a time sufficient to produce aromatic carboxylic acid compounds.

The aromatic carboxylic acid compounds that are made can include terephthalic acid, naphthalic acid, thiophene dicarboxylic acid, pyridine dicarboxylic acid, carbazole dicarboxylic acid, and dibenzothiophene dicarboxylic acid. The metal hydroxide and at least one carboxylate are often provided in a solvent such as water or an alcohol such as methanol, ethanol, propanol and butanol which is removed from the mixture before the carbon dioxide is added. The heat used in the reaction will depend upon the compound being synthesized and may range from ambient temperature to about 400° C. or in some instances from about 200° C. to 300° C. or from 100° C. to 300° C. The metal hydroxides that are used include lithium hydroxide, sodium hydroxide, potassium hydroxide, rubidium hydroxide, cesium hydroxide, magnesium hydroxide and calcium hydroxide. The carboxylate includes cations selected from lithium, sodium, potassium, rubidium, cesium, magnesium, and calcium and anions selected from formates, acetates, dicarboxylates and tricarboxylates. The metal hydroxide may be at a mole ratio of metal hydroxide to aromatic compound or an aromatic compound with at least one carboxylic group is from about 1:1 to 2:1, 1:0.1 to 1:1, 1:0.1 to 1:0.5 or 0.1:1 to 1:1. The reaction time is sufficient to produce the aromatic carboxylic acid compound is from about 1 second to 24 hours, 1 minute to 12 hours, 1 minute to 6 hours, or 1 minute to 1 hour. The process may be continuous, semi-batch or batch reaction process. In some instances, the aromatic carboxylic acid compound is furan-2,5-dicarboxylatye. The acetates may be selected from propionate, butyrate, isobutyrate and lactate the dicarboxylates are selected from oxalate, malonate, succinate and adipate and the tricarboxylates are selected from citrate and isocitrate.

DETAILED DESCRIPTION

A major impediment to synthesizing compounds from carbon dioxide is the difficulty of forming carbon-carbon (C—C) bonds efficiently. $CO_2$ reacts readily with carbon-centered nucleophiles but generating these intermediates has previously required high-energy reagents (e.g. highly reducing metals or strong organic bases), carbon-heteroatom bonds, and/or relatively acidic C—H bonds. These requirements negate the environmental benefit of using $CO_2$ as a substrate and limit the chemistry to low-volume targets. International application WO2016/153937A1 discusses prior art methods of producing FDCA as well as a method of producing FDCA by using a carbonate.

This disclosure provides for the use of inexpensive starting materials such as potassium hydroxide and potassium acetate to be used in the reaction of aromatic compounds such as benzene or aromatic compounds with a carboxylic group such as furoic acid to aromatic dicarboxylic acids. These hydroxides and acetates are much less expensive than prior art reactions that use reagents such as cesium carbonate, potassium carbonate and potassium isobutyrate. For example, potassium hydroxide costs about 10 times less than cesium carbonate on a mole basis with similar performance. The FDCA that is produced with this method can then be used in making polymers.

The aromatic dicarboxylic acids that can be prepared by the process disclosed herein include terephthalic acid, naphthalic acid, thiophene dicarboxylic acid, pyridine dicarboxylic acid, carbazole dicarboxylic acid, and dibenzothiophene dicarboxylic acid. The metal hydroxides that can be used include lithium hydroxide, sodium hydroxide, potassium hydroxide, rubidium hydroxide, cesium hydroxide, magnesium hydroxide and calcium hydroxide and mixtures thereof. The carboxylates that can be used include cations selected from lithium, sodium, potassium, rubidium, cesium, magnesium, and calcium and anions selected from formates, acetates selected from propionate, butyrate, isobutyrate and lactate, dicarboxylates selected from oxalate, malonate, succinate and adipate and tricarboxylates selected from citrate and isocitrate.

In order to more fully illustrate the invention, the following examples are set forth. It is to be understood that the examples are only by way of illustration and are not intended as an undue limitation on the broad scope of the invention as set forth in the appended claims.

EXAMPLE 1

A water solution of potassium hydroxide (1.05 equiv.) was added to furoic acid. The water was removed by a rotary evaporator at 120° C. for 2 h producing a white solid. In a nitrogen atmosphere, the solid was then combined with potassium hydroxide (1 equiv.) and potassium acetate (0.37 equiv.). The solids were crushed and mixed with a mortar and pestle to form a powder. The powder was loaded into a glass lined 75 mL autoclave. The autoclave was backfilled 3× with carbon dioxide then filled with $CO_2$ (220 psig). The autoclave was heated to 280° C. for 1-4 h. After the allotted time, the autoclave was cooled for 30 min, and the reaction was vented into a hood. A dark solid resulted, which was analyzed by $^1H$ and $^{13}C$ NMR spectroscopy (Table 1).

TABLE 1

| Time (h) | $CO_2$ added at 25° C. (psig) | Potassium acetate (mol equivalent) | Conversion of Furoic Acid (%) | % Selectivity to FDCA salt | % Selectivity to Malonate | % Selectivity to Other |
|---|---|---|---|---|---|---|
| 1 | 220 | 0.37 | 30.6 | 95.0 | 0.38 | 4.5 |
| 2.75 | 220 | 0.37 | 80.5 | 87.1 | 6.5 | 6.2 |
| 4 | 220 | 0.37 | 87.6 | 81.9 | 9.6 | 9.4 |

Example 1 shows the progression of the reaction with potassium hydroxide and potassium acetate over time.

EXAMPLE 2

A water solution of potassium carbonate (1.05 equiv.) was added to furoic acid. The water was removed by a rotary evaporator at 120° C. for 2 h producing a white solid. In a nitrogen atmosphere, the solid was then combined with potassium carbonate (1 equiv.) and potassium acetate (0.15-1.66 equivalents). The solids were crushed and mixed with a mortar and pestle to form a powder. The powder was loaded into a glass lined 75 mL autoclave. The autoclave was backfilled 3× with carbon dioxide then filled with $CO_2$ (120 psig). The autoclave was heated to 280° C. for 1 h. After 1 h, the autoclave was cooled for 30 min, and the reaction was vented into a hood. A dark solid resulted, which was analyzed by $^1H$ and $^{13}C$ NMR spectroscopy (FIG. 2).

TABLE 2

| Time (h) | $CO_2$ added at 25° C. (psig) | Potassium acetate (mol equivalent) | Conversion of Furoic Acid (%) | % Selectivity to FDCA salt | % Selectivity to Malonate | % Selectivity to Other |
|---|---|---|---|---|---|---|
| 1 | 120 | 0.15 | 23 | 86 | 5 | 9.4 |
| 1 | 120 | 0.37 | 72 | 69 | 13 | 17 |
| 1 | 120 | 0.77 | 73 | 48 | 23 | 28 |
| 1 | 120 | 1.66 | 94 | 20 | 45 | 35 |

In Example 2, the effectiveness of the use of potassium acetate is shown when used in combination with potassium carbonate.

EXAMPLE 3

A water solution of potassium carbonate (1.05 equiv.) was added to furoic acid. The water was removed by a rotary evaporator at 120° C. for 2 h producing a white solid. In a nitrogen atmosphere, the solid was then combined with potassium hydroxide (1 equiv.) and potassium acetate (0.37 equiv.). The solids were crushed and mixed with a mortar and pestle to form a powder. The powder was loaded into a glass lined 75 mL autoclave. The autoclave was backfilled 3× with carbon dioxide then filled with $CO_2$ (20-220 psig). The autoclave was heated to 280° C. for 1 h. After the allotted time, the autoclave was cooled for 30 min, and the reaction was vented into a hood. A dark solid resulted, which was analyzed by $^1H$ and $^{13}C$ NMR spectroscopy (Table 3).

TABLE 3

| Time (h) | $CO_2$ added at 25° C. (psig) | Potassium acetate (mol equivalent) | Conversion of Furoic Acid (%) | % Selectivity to FDCA salt | % Selectivity to Malonate | % Selectivity to Other |
|---|---|---|---|---|---|---|
| 1 | 20 | 0.37 | 64 | 52 | 18 | 30 |
| 1 | 80 | 0.37 | 72 | 69 | 13 | 17 |

TABLE 3-continued

| Time (h) | $CO_2$ added at 25° C. (psig) | Potassium acetate (mol equivalent) | Conversion of Furoic Acid (%) | % Selectivity to FDCA salt | % Selectivity to Malonate | % Selectivity to Other |
| --- | --- | --- | --- | --- | --- | --- |
| 1 | 150 | 0.37 | 65 | 82 | 8.3 | 9.3 |
| 1 | 220 | 0.37 | 69 | 86 | 7.2 | 6.6 |

In Example 3 is shown the increased selectivity to the desired product as the pressure of the carbon dioxide is increased.

EXAMPLE 4

A water solution of potassium hydroxide (2.05 equiv.) and potassium acetate (0.37 equiv.) was added to furoic acid. The water was removed by a rotary evaporator at 120° C. for 4 h producing a white solid. In a nitrogen atmosphere, the solid was then crushed and mixed with a mortar and pestle to form a powder. The powder was loaded into a glass lined 75 mL autoclave. The autoclave was backfilled 3× with carbon dioxide then filled with $CO_2$ (220 psig). The autoclave was heated to 280° C. for 2 h. After the allotted time, the autoclave was cooled for 30 min, and the reaction was vented into a hood. A dark solid resulted, which was analyzed by $^1H$ and $^{13}C$ NMR spectroscopy (Table 4).

TABLE 4

| Time (h) | $CO_2$ added at 25° C. (psig) | Potassium acetate (mol equivalent) | Conversion of Furoic Acid (%) | % Selectivity to FDCA salt | % Selectivity to Malonate | % Selectivity to Other |
| --- | --- | --- | --- | --- | --- | --- |
| 2 | 220 | 0.37 | 40 | 92 | 4.3 | 2.7 |

Example 4 shows a variation in the process where the hydroxide and carboxylate are added at the beginning of the process followed by the removal of water and then the addition of carbon dioxide under reaction conditions.

EXAMPLE 5

A methanol solution of potassium hydroxide (1.05 equiv.) was added to furoic acid. The methanol was removed by a rotary evaporator at 120° C. for 2 h producing a white solid. In a nitrogen atmosphere, the solid was then combined with potassium hydroxide (1 equiv.) and potassium acetate (0.37 equiv.). The solids were crushed and mixed with a mortar and pestle to form a powder. The powder was loaded into a glass lined 75 mL autoclave. The autoclave was backfilled 3× with carbon dioxide then filled with $CO_2$ (220 psig). The autoclave was heated to 280° C. for 1 h. After the allotted time, the autoclave was cooled for 30 min, and the reaction was vented into a hood. A dark solid resulted, which was analyzed by $^1H$ and $^{13}C$ NMR spectroscopy (Table 5).

TABLE 5

| Time (h) | $CO_2$ added at 25° C. (psig) | Potassium acetate (mol equivalent) | Conversion of Furoic Acid (%) | % Selectivity to FDCA salt | % Selectivity to Malonate | % Selectivity to Other |
| --- | --- | --- | --- | --- | --- | --- |
| 1 | 220 | 0.37 | 55 | 90 | 8 | 2 |

In Example 5 is shown the process with the use of methanol instead of water as the solvent.

EXAMPLE 6

A methanol solution of potassium hydroxide (1.05 equiv.) was added to furoic acid. The methanol was removed by a rotary evaporator at 120° C. for 2 h producing a white solid. In a nitrogen atmosphere, the solid was then combined with potassium hydroxide (0.56 equiv.) and potassium acetate (0.37 equiv.). The solids were crushed and mixed with a mortar and pestle to form a powder. The powder was loaded into a glass lined 75 mL autoclave. The autoclave was backfilled 3× with carbon dioxide then filled with $CO_2$ (220 psig). The autoclave was heated to 280° C. for 0.5 h. After the allotted time, the autoclave was cooled for 30 min, and the reaction was vented into a hood. A dark solid resulted, which was analyzed by $^1H$ and $^{13}C$ NMR spectroscopy (Table 6).

TABLE 6

| Time (h) | $CO_2$ added at 25° C. (psig) | Potassium acetate (mol equivalent) | Conversion of Furoic Acid (%) | % Selectivity to FDCA salt | % Selectivity to Malonate | % Selectivity to Other |
| --- | --- | --- | --- | --- | --- | --- |
| 0.5 | 220 | 0.37 | 42 | 89 | 7.5 | 3.5 |

In Example 6, a reduced amount of potassium acetate is used with a shortened reaction time that showed the reaction to still be effective in producing a high product yield.

EXAMPLE 7

A water solution of potassium hydroxide (1.05 equiv.) was added to furoic acid. The water was removed by a rotary evaporator at 120° C. for 2 h producing a white solid. In a nitrogen atmosphere, the solid was then combined with potassium hydroxide (1 equiv.) and potassium acetate (0.37 equiv.). The solids were crushed and mixed with a mortar and pestle to form a powder. The powder was loaded into a glass lined 75 mL autoclave. The autoclave was backfilled 3× with carbon dioxide then filled with $^{13}CO_2$ (80 psig). The autoclave was heated to 280° C. for 1 h. After the allotted time, the autoclave was cooled for 30 min, and the reaction was vented into a hood. A dark solid resulted, which was analyzed by $^1H$ and $^{13}C$ NMR spectroscopy (Table 7), and mass spectroscopy of the solid indicated 93% incorporation of $^{13}C$ into the FDCA product.

TABLE 7

| Time (h) | $CO_2$ added at 25° C. (psig) | Potassium acetate (mol equivalent) | Conversion of Furoic Acid (%) | % Selectivity to FDCA salt | % Selectivity to Malonate | % Selectivity to Other |
| --- | --- | --- | --- | --- | --- | --- |
| 1 | 80 | 0.37 | 23 | 92 | 8.0 | 0 |

In Example 7 is shown evidence that carbon from the carbon dioxide reagent is incorporated into the compound.

Specific Embodiments

While the following is described in conjunction with specific embodiments, it will be understood that this description is intended to illustrate and not limit the scope of the preceding description and the appended claims.

A first embodiment of the invention is a method for synthesizing an aromatic carboxylic acid compound comprising providing an aromatic compound or an aromatic compound with at least one carboxylic group; providing a metal hydroxide and at least one carboxylate to produce a mixture; and adding carbon dioxide to the mixture under pressures from about atmospheric to 1000 psig and sufficient heat for a time sufficient to produce aromatic carboxylic acid compound. An embodiment of the invention is one, any or all of prior embodiments in this paragraph up through the first embodiment in this paragraph wherein the aromatic carboxylic acid compound is selected from benzoic acid, toluic acid, furoic acid, 2,5-furandicarboxylic acid, terephthalic acid, naphthalic acid, thiophene dicarboxylic acid, pyridine dicarboxylic acid, carbazole dicarboxylic acid, and dibenzothiophene dicarboxylic acid. An embodiment of the invention is one, any or all of prior embodiments in this paragraph up through the first embodiment in this paragraph wherein the metal hydroxide and the at least one carboxylate are in a solvent wherein the solvent is removed prior to the carbon dioxide being added to the mixture. An embodiment of the invention is one, any or all of prior embodiments in this paragraph up through the first embodiment in this paragraph wherein the solvent is water or an alcohol. An embodiment of the invention is one, any or all of prior embodiments in this paragraph up through the first embodiment in this paragraph wherein the alcohol is selected from methanol, ethanol, propanol and butanol. An embodiment of the invention is one, any or all of prior embodiments in this paragraph up through the first embodiment in this paragraph wherein the sufficient heat is from ambient temperature to about 400° C. An embodiment of the invention is one, any or all of prior embodiments in this paragraph up through the first embodiment in this paragraph wherein the metal hydroxide is selected from lithium hydroxide, sodium hydroxide, potassium hydroxide, rubidium hydroxide, cesium hydroxide, magnesium hydroxide and calcium hydroxide. An embodiment of the invention is one, any or all of prior embodiments in this paragraph up through the first embodiment in this paragraph wherein the metal hydroxide is potassium hydroxide. An embodiment of the invention is one, any or all of prior embodiments in this paragraph up through the first embodiment in this paragraph wherein the carboxylate consists of cations selected from lithium, sodium, potassium, rubidium, cesium, magnesium, and calcium and anions selected from formates, acetates, dicarboxylates and tricarboxylates. An embodiment of the invention is one, any or all of prior embodiments in this paragraph up through the first embodiment in this paragraph wherein the temperatures are from about 200° C. to 300° C. An embodiment of the invention is one, any or all of prior embodiments in this paragraph up through the first embodiment in this paragraph wherein the metal hydroxide provided is at a mole ratio of metal hydroxide to aromatic compound or an aromatic compound with at least one carboxylic group is from about 1:1 to 2:1. An embodiment of the invention is one, any or all of prior embodiments in this paragraph up through the first embodiment in this paragraph wherein the metal hydroxide and the carboxylate are at a mole ratio from about 1:0.1 to 1:1 or 0.1 to 1:1. An embodiment of the invention is one, any or all of prior embodiments in this paragraph up through the first embodiment in this paragraph wherein the time sufficient to produce the aromatic carboxylic acid compound is from about 1 second to 24 hours. An embodiment of the invention is one, any or all of prior embodiments in this paragraph up through the first embodiment in this paragraph wherein the synthesis of the aromatic carboxylic acid compound is a continuous, semi-batch or batch reaction process. An embodiment of the invention is one, any or all of prior embodiments in this paragraph up through the first embodiment in this paragraph wherein the aromatic carboxylic acid compound is furan-2, 5-dicarboxylate. An embodiment of the invention is one, any or all of prior embodiments in this paragraph up through the first embodiment in this paragraph wherein the anions are selected from propionate, butyrate, isobutyrate or lactate. An embodiment of the invention is one, any or all of prior embodiments in this paragraph up through the first embodiment in this paragraph wherein the dicarboxylates are selected from oxalate, malonate, succinate and adipate. An embodiment of the invention is one, any or all of prior embodiments in this paragraph up through the first embodiment in this paragraph wherein the tricarboxylates are selected from citrate and isocitrate.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A method for synthesizing an aromatic carboxylic acid compound comprising
   a. providing an aromatic compound or an aromatic compound with at least one carboxylic group;
   b. providing a metal hydroxide and at least one carboxylate to produce a mixture; and
   c. adding carbon dioxide to the mixture under pressures from about atmospheric to 1000 psig and sufficient heat for a time sufficient to produce an aromatic carboxylic acid compound.

2. The method of claim 1 wherein said aromatic carboxylic acid compound is selected from benzoic acid, toluic acid, furoic acid, furan dicarboxylic acid, 2,5-furan dicarboxylic acid, terephthalic acid, naphthalic acid, thiophene dicarboxylic acid, pyridine dicarboxylic acid, carbazole dicarboxylic acid, and dibenzothiophene dicarboxylic acid.

3. The method of claim 1 wherein said metal hydroxide and said at least one carboxylate are in a solvent wherein said solvent is removed prior to said carbon dioxide being added to the mixture.

4. The method of claim 3 wherein said solvent is water or an alcohol.

5. The method of claim 4 wherein said alcohol is selected from methanol, ethanol, propanol and butanol.

6. The method of claim 1 wherein said sufficient heat is from ambient temperature to about 400° C.

7. The method of claim 1 wherein said metal hydroxide is selected from lithium hydroxide, sodium hydroxide, potassium hydroxide, rubidium hydroxide, cesium hydroxide, magnesium hydroxide and calcium hydroxide.

8. The method of claim 1 wherein said metal hydroxide is potassium hydroxide.

9. The method of claim 1 wherein said carboxylate consists of cations selected from lithium, sodium, potassium, rubidium, cesium, magnesium, and calcium and anions selected from formates, acetates, dicarboxylates and tricarboxylates.

10. The method of claim 1 wherein said temperatures are from about 200° C. to 300° C.

11. The method of claim 1 wherein said metal hydroxide provided in step 1b is at a mole ratio of metal hydroxide to aromatic compound or an aromatic compound with at least one carboxylic group is from about 1:1 to 2:1.

12. The method of claim 1 wherein said metal hydroxide and said carboxylate are at a mole ratio from about 1:0.1 to 1:1.

13. The method of claim 1 wherein said time sufficient to produce the aromatic carboxylic acid compound is from about 1 second to 24 hours.

14. The method of claim 1 wherein said synthesis of the aromatic carboxylic acid compound is a continuous, semi-batch or batch reaction process.

15. The method of claim 1 wherein the aromatic carboxylic acid monomer is furan-2,5-dicarboxylate.

16. The method of claim 9 wherein said anions are propionate, butyrate, isobutyrate or lactate.

17. The method of claim 9 wherein said dicarboxylates are selected from oxalate, malonate, succinate and adipate.

18. The method of claim 9 wherein said tricarboxylates are selected from citrate and isocitrate.

* * * * *